United States Patent
Musso

(10) Patent No.: US 12,253,511 B2
(45) Date of Patent: Mar. 18, 2025

(54) SYSTEM AND METHOD FOR TESTING CEMENT

(71) Applicant: ARAMCO SERVICES COMPANY, Houston, TX (US)

(72) Inventor: Simone Musso, Houston, TX (US)

(73) Assignee: SAUDI ARABIAN OIL COMPANY, Dhahran (SA)

(*) Notice: Subject to any disclaimer, the term of this patent is extended or adjusted under 35 U.S.C. 154(b) by 698 days.

(21) Appl. No.: 17/316,280

(22) Filed: May 10, 2021

(65) Prior Publication Data
US 2021/0356452 A1 Nov. 18, 2021

Related U.S. Application Data

(60) Provisional application No. 63/025,466, filed on May 15, 2020.

(51) Int. Cl.
*G01N 33/38* (2006.01)
*G01N 3/12* (2006.01)

(52) U.S. Cl.
CPC .......... *G01N 33/383* (2013.01); *G01N 3/12* (2013.01); *G01N 2203/0048* (2013.01);
(Continued)

(58) Field of Classification Search
CPC ............ G01N 33/383; G01N 3/12; G01N 2203/0048; G01N 2203/0094;
(Continued)

(56) References Cited

U.S. PATENT DOCUMENTS

| | | | |
|---|---|---|---|
| 6,817,238 B2 * | 11/2004 | Go Boncan ......... | G01N 33/383 73/866 |
| 6,918,292 B2 * | 7/2005 | Go Boncan ......... | G01N 33/383 73/866 |

(Continued)

FOREIGN PATENT DOCUMENTS

| WO | WO-2019055043 A1 * | 3/2019 | ........... E21B 47/003 |
|---|---|---|---|
| WO | 2019094025 A1 | 5/2019 | |
| WO | WO-2019221759 A1 * | 11/2019 | |

OTHER PUBLICATIONS

M.E. Chenevert, Chemical Shrinkage Properties of Oilfield Cements, Society of Petroleum Engineers, SPE Drilling Engineering, Mar. 1991, pp. 37-43 (Year: 1991).*

(Continued)

*Primary Examiner* — Marrit Eyassu
(74) *Attorney, Agent, or Firm* — Osha Bergman Watanabe & Burton LLP

(57) ABSTRACT

A method of measuring cement volumetric changes includes loading a sample cement into a flexible container and surrounding the flexible container by a column of fluid in a chamber. The temperature of the column of fluid is adjusted to a cement setting temperature, and the sample cement is allowed to set over several hours. The pressure of the column of fluid is adjusted to a test pressure. The temperature of the column of fluid in the chamber is adjusted to induce volumetric changes in the set cement. As the volume of the set cement changes, fluid volume adjustments are applied to the column of fluid in the chamber to maintain the pressure of the column of fluid in the chamber constant at the test pressure. The volumetric changes in the set cement are determined from the fluid volume adjustments applied to the column of fluid in the chamber.

20 Claims, 7 Drawing Sheets

(52) U.S. Cl.
CPC ............... *G01N 2203/0094* (2013.01); *G01N 2203/0222* (2013.01); *G01N 2203/0232* (2013.01); *G01N 2203/025* (2013.01)

(58) Field of Classification Search
CPC ... G01N 2203/0222; G01N 2203/0232; G01N 2203/025
USPC .......................................................... 73/37
See application file for complete search history.

(56) References Cited

U.S. PATENT DOCUMENTS

| | | | | |
|---|---|---|---|---|
| 7,240,545 | B1* | 7/2007 | Jennings | G01F 22/00 73/866 |
| 9,557,315 | B2 | 1/2017 | Kats et al. | |
| 9,594,009 | B2* | 3/2017 | Meadows | G01N 3/12 |
| 2003/0033893 | A1 | 2/2003 | Go Boncan et al. | |
| 2006/0225523 | A1 | 10/2006 | Reddy et al. | |
| 2008/0168848 | A1 | 7/2008 | Funkhouser et al. | |
| 2009/0084189 | A1* | 4/2009 | McMechan | G01N 3/12 73/803 |
| 2011/0061525 | A1* | 3/2011 | Gray | G01N 3/24 92/75 |
| 2013/0153221 | A1* | 6/2013 | Loiseau | E21B 33/14 106/668 |
| 2013/0192382 | A1* | 8/2013 | Bois | G01N 33/383 73/803 |
| 2017/0108456 | A1 | 4/2017 | Alizadeh et al. | |
| 2017/0205388 | A1 | 7/2017 | Thomas et al. | |

OTHER PUBLICATIONS

Suhascaryo Nur, The Effect of Expanding Additives to Improve Cement Isolation Strength to 2500C and 2000C psi Conditions, Apr. 2005, Proceedings World Geothermal Congress 2005, Antalya Turkey, 24-29 (Year: 2005).*

Chenevert, M.E., and B.K. Shrestha, "Chemical Shrinkage Properties of Oilfield Cements (includes associated paper 23477)", Paper No. SPE-16654-PA, SPE Drilling Engineering, vol. 6, Issue 01, Mar. 1991, 37-43 (8 pages).

International Search Report and Written Opinion of the International Searching Authority issued in corresponding International Application No. PCT/US2021/032531, mailed on Sep. 6, 2021 (16 pages).

Nur, S., et al., "The Effect of Expanding Additives to Improve Cement Isolation Strength to 250oC and 2000 psi Conditions", Proceedings 2005 World Geothermal Congress, pp. 1-14, Apr. 29, 2005 (14 pages).

* cited by examiner

SYSTEM AND METHOD FOR TESTING CEMENT

FIELD

The disclosure relates generally to testing of cement formulations.

BACKGROUND

Cement is used extensively in oil and gas wells to support casings, prevent fluid leakage to the surface, and isolate producing zones from water bearing zones. Cement may be placed between two casings or between a casing and surrounding formation. After a cement sheath has been placed in the well, dimensional changes can occur in the cement sheath. These dimensional changes can result in microannuli at the casing-cement interface or formation-cement interface. Microannuli at these interfaces can result in unwanted leakage paths in the well and communication between zones that should normally be isolated.

Cement integrity under downhole conditions may be controlled to some degree by design of the cement formulation. For example, it has been proposed to use expansive cement formulations to combat cement shrinkage that could result in microannuli.

Cement testing is used to discover cement formulations with certain desired properties. Currently, the American Petroleum Institute (API) recommends use of circular expansion molds to research and test expansive cement formulations. A typical circular expansion mold includes a ring mold and a micrometer to measure a gap on the mold. The ring mold has an inner ring and an outer ring arranged to simulate an annulus between two casings or between a casing and a borehole wall. To test a cement formulation, a cement slurry having the cement formulation is poured into the annulus in the ring mold. The cement volume is then measured by using the micrometer to measure the gap on the mold. After measuring this initial cement volume, the ring mold with the cement slurry is placed in a curing chamber or consistometer. After the cement has cured, the gap on the mold is again measured using the micrometer. The difference in micrometer measurements indicates the volumetric change in the cement. Current circular expansion mold testing kits do not allow for interactive temperature and pressure adjustments during cement testing. Moreover, it is difficult to take numerous data measurements in real-time without compromising the integrity of the test.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method of testing cement includes loading a cement slurry into a flexible container. The flexible container is disposed in a column of fluid in a chamber. The pressure of the column of fluid in the chamber is adjusted to a test pressure. The temperature of the column of fluid in the chamber is adjusted to within a first temperature range and maintained within this range for a first time period in which the cement slurry sets to form a set cement. The temperature of the column of fluid in the chamber is adjusted to within a second temperature range that is greater than the first temperature range. Over a second time period following the first time period, fluid volume adjustments are applied to the column of fluid in the chamber to maintain the pressure of the column of fluid in the chamber substantially constant at the test pressure. Volumetric changes in the set cement over at least a portion of the second time period are determined based on the fluid volume adjustments applied to the column of fluid in the chamber.

The cement slurry may include a hydraulic cement and an expanding additive. The expanding additive may trigger expansion of the set cement when the set cement has a temperature in the second temperature range. The fluid volume adjustments may be applied to the column of fluid by withdrawing fluid from the chamber as the set cement expands. Withdrawing fluid from the chamber as the set cement expands may include measuring a pressure of fluid in the chamber and controlling a pump in communication with the chamber to withdraw fluid from the chamber based on a difference between the measured pressure and the test pressure. Volumetric changes in the set cement may be determined from a volume of fluid withdrawn from the chamber over at least a portion of the second time period.

The method may include, during an initial portion of the second time period, increasing the temperature of the column of fluid in the chamber to a temperature at which the expanding additive starts to hydrate. The method may include maintaining the temperature of the column of fluid in the chamber at the temperature at which the expanding additive starts to hydrate for a remaining portion of the second time period. The fluid volume adjustments may be applied to the column of fluid by selectively injecting fluid into and withdrawing fluid from the chamber by a syringe pump. The temperature of the column of fluid in the chamber may be maintained within the second temperature range over the second time period. The pressure of the column of fluid in the chamber may be adjusted to the set pressure by pumping fluid into the column of fluid at the test pressure.

A system for testing cement includes a flexible mold to hold a sample cement, a chamber to hold a column of fluid around the flexible mold, a heater arranged to provide heat to the chamber, a pump in fluid communication with the chamber, and a pump controller to adjust a flow rate and flow direction of the pump in response to a difference in pressure between the chamber and a pressure setpoint. The flexible mold may include a tube having a wall made of a flexible material. The flexible material may be an elastomeric material. The flexible mold may include permeable plugs removably mounted at opposite ends of the tube. Alternatively, the flexible mold may include impermeable plugs removably mounted at opposite ends of the tube. The pump may be a syringe pump. The system may include a temperature controller to adjust a heat output of the heater in response to a difference in temperature between the chamber and a temperature setpoint. The system may include at least one temperature sensor arranged to monitor the temperature within the chamber. The temperature controller may be in communication with the at least one temperature sensor. The system may include at least one pressure sensor arranged to monitor the pressure within the chamber. The pump controller may be in communication with the at least one pressure sensor.

The foregoing general description and the following detailed description are exemplary of the invention and are intended to provide an overview or framework for understanding the nature of the invention as it is claimed. The accompanying drawings are included to provide further understanding of the invention and are incorporated in and constitute a part of the specification. The drawings illustrate various embodiments of the invention and together with the description serve to explain the principles and operation of the invention.

Other aspects and advantages of the claimed subject matter will be apparent from the following description and the appended claims.

BRIEF DESCRIPTION OF DRAWINGS

The following is a description of the figures in the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

Figure 1:
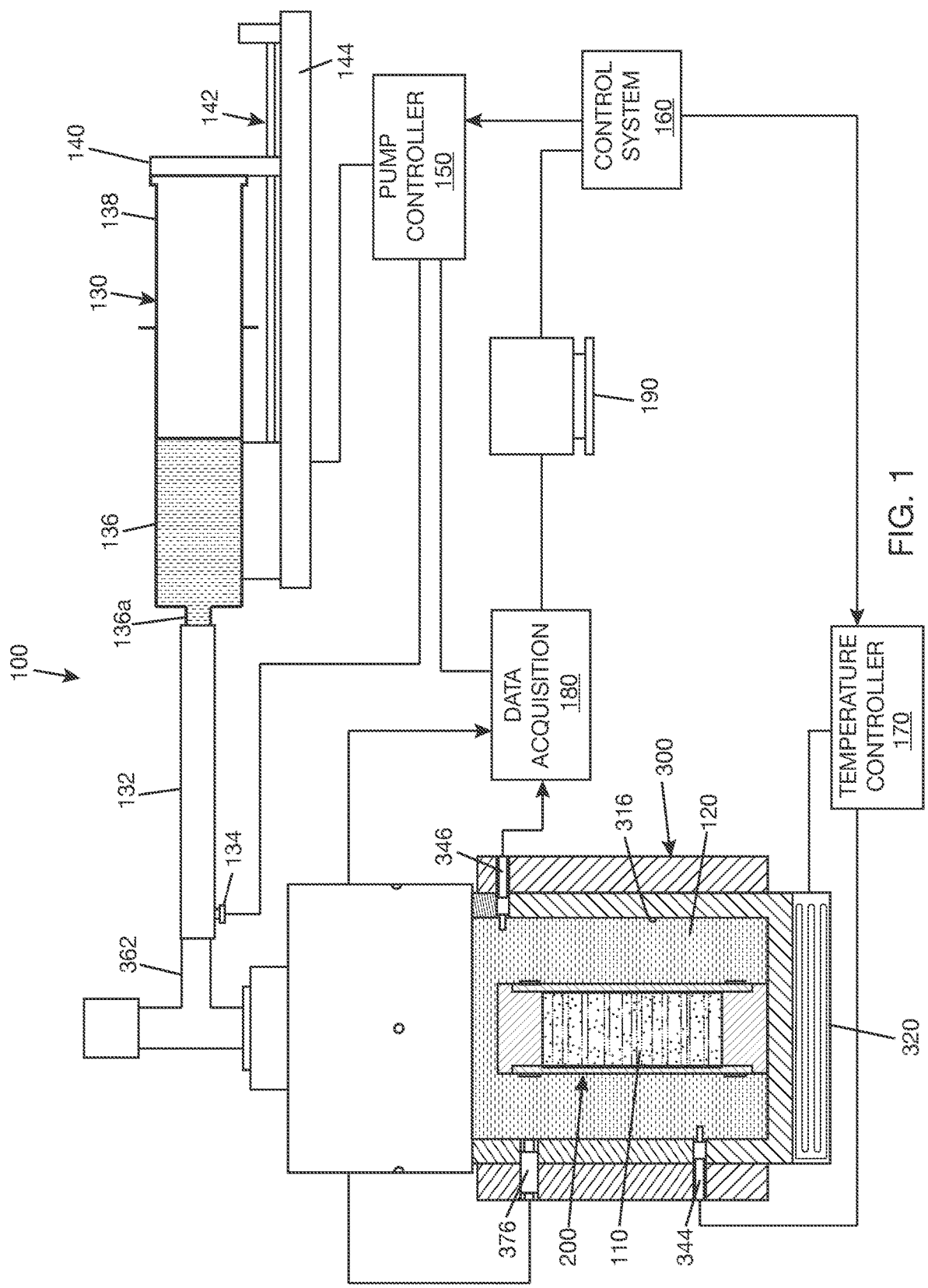
FIG. 1 shows a schematic of a system for testing a sample cement in accordance with one or more embodiments.

In the following detailed description, certain specific details are set forth in order to provide a thorough understanding of various disclosed implementations and embodiments. However, one skilled in the relevant art will recognize that implementations and embodiments may be practiced without one or more of these specific details, or with other methods, components, materials, and so forth. In other instances, well known features or processes associated with the hydrocarbon production systems have not been shown or described in detail to avoid unnecessarily obscuring descriptions of the implementations and embodiments. For the sake of continuity, and in the interest of conciseness, same or similar reference characters may be used for same or similar objects in multiple figures.

Figure 2A:
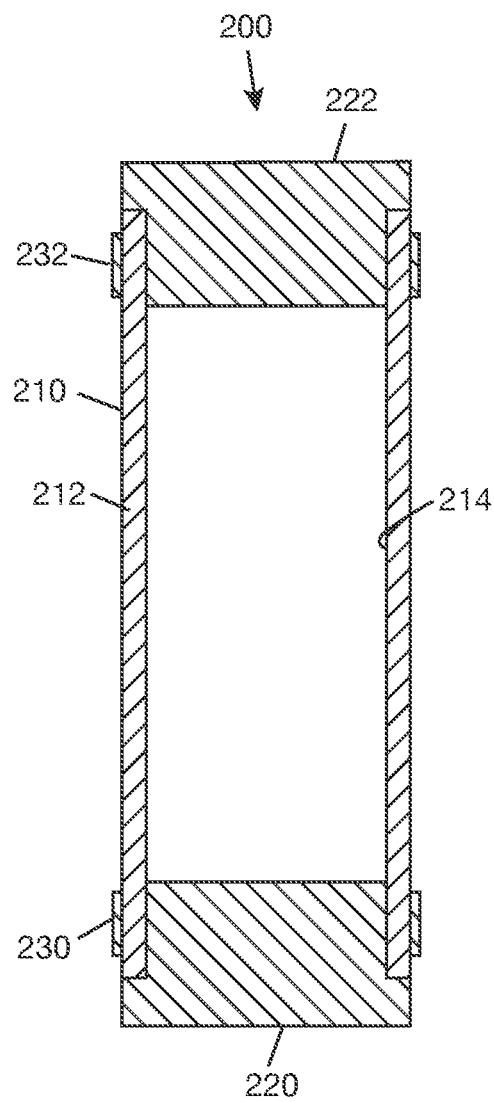
FIG. 2A shows a cross-sectional view of a flexible mold in accordance with one or more embodiments.
Figure 2B:
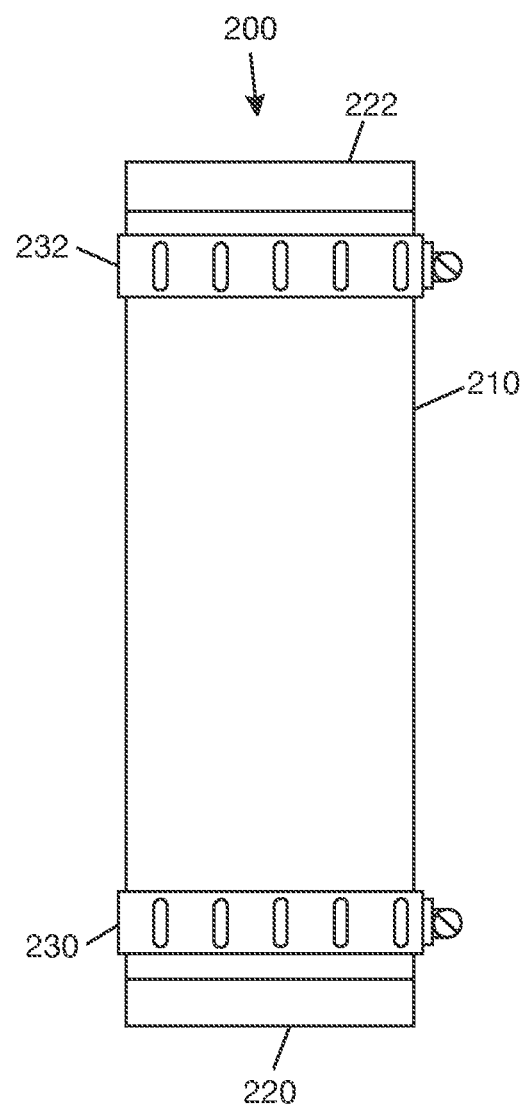
FIG. 2B shows an elevation view of the flexible mold shown in FIG. 2A in accordance with one or more embodiments.

FIG. 1 shows a system 100 for testing a sample cement according to one illustrative implementation. System 100 can be used to measure volumetric changes in sample cement under certain high pressure and high temperature conditions. System 100 includes a flexible mold 200 containing a sample cement 110 to be tested. As shown more clearly in FIGS. 2A and 2B, flexible mold 200 includes a tube (or sleeve) 210 having a wall 212 made of a flexible material. Flexible wall 212 can radially expand or contract under applied pressure. In one implementation, the material of wall 212 is also impermeable. In a non-limiting example, wall 212 is made of an elastomeric material. Examples of suitable elastomeric materials are synthetic polyisoprene, neoprene, polybutadiene, styrene-butadiene rubber, nitrile rubber, hydrogenated nitrile rubber, polyacrylic rubber, silicone rubber, fluorosilicone rubber, and perfluoroelastomers. Tube 210 has a bore 214 circumscribed by wall 212. Bore 214 holds a sample cement (110 in FIG. 1) during cement testing. Flexible mold 200 includes plugs 220, 222 that are inserted at opposite ends of tube 210. Plugs 220, 222 may be retained at their respective ends of tube 210 by any suitable method. As an example, plugs 220, 222 may be retained at the ends of tube 210 by means of hose clamps 230, 232 (in FIG. 2B) that wrap around the end portions of tube 210 circumscribing plugs 220, 222, respectively.

Plugs 220, 222 are typically not flexible (or are typically rigid). In one example, plugs 220, 222 may be impermeable plugs that do not allow liquid to pass through. Impermeable plugs will prevent external fluid form reaching a sample cement inside bore 214 and may be used when it is desired to simulate a casing-to-casing cement bond in the cement testing procedure. Impermeable plugs may be plugs made of metal or an alloy or other impermeable material that can withstand high temperatures. Examples of suitable impermeable materials are brass and stainless steel. In another example, plugs 220, 222 may be permeable plugs that allow liquid to pass through. Permeable plugs will allow external fluid to reach a sample cement inside bore 214 and may be used when it is desired to simulate a casing-to-formation cement bond in the cement testing procedure. Permeable plugs may be made of porous ceramic or other porous material that can withstand high temperatures. Alternatively, permeable plugs may be provided by forming orifices in impermeable materials.

Returning to FIG. 1, system 100 includes a test chamber 300 containing flexible mold 200 and a column of fluid 120. Test chamber 300 is connected to a syringe pump 130, which can be operated to inject fluid into test chamber 300 or withdraw fluid from test chamber 300. As shown more clearly in FIG. 3A, test chamber 300 includes a vessel 310 having a bottom wall 312 and a sidewall 314 defining a chamber 316. Chamber 316 is large enough to hold a flexible mold (200 in FIG. 1) and a column of fluid (120 in FIG. 1) around the flexible mold. Preferably, vessel 310 is a high-pressure, high-temperature (HPHT) vessel (or high-temperature, high-pressure (HTHP) vessel). In one example, a HPHT (or HTHP) vessel may be a vessel that can withstand temperatures up to 200° C. and pressures up to 1378 bars (20,000 psi). HPHT vessel that can withstand temperatures higher than 200° C. and pressures higher than 1378 bar could be used as well. In general, vessel 310 is able to withstand the temperature and pressure conditions required for testing a sample cement. The pressure and temperature ratings of vessel 310 will typically be dictated by the material and thickness of the vessel walls 312, 314.

Figure 3A:
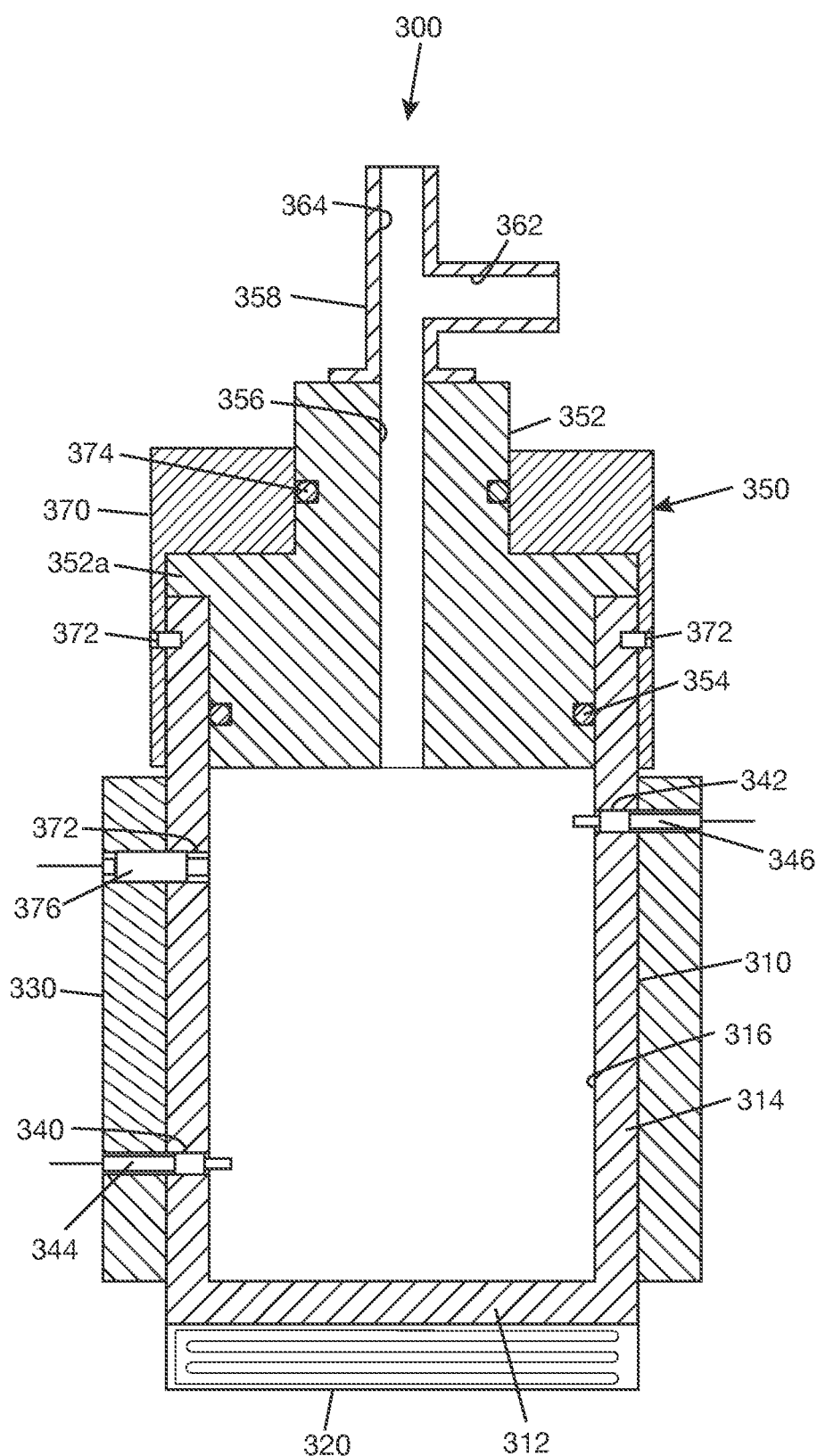
FIG. 3A shows a cross-sectional view of a test chamber in accordance with one or more embodiments.

Test chamber 300 includes a heater 320 arranged to heat the contents of chamber 316. FIG. 3A shows heater 320 disposed adjacent to bottom wall 312. Alternatively, heater 320 could be disposed adjacent to sidewall 314 and may circumscribe sidewall 314. Alternatively, heaters could be disposed adjacent to both walls 312, 314. In one example, an insulation jacket 330 is disposed around sidewall 314 to assist in maintaining a desired temperature inside chamber 316. Alternatively, a jacket heater (not shown) that wraps around vessel 310 may be used in place of a separate heater 320 and insulation jacket 330. In general, any suitable heating arrangement that is capable of heating vessel 310 and the contents of chamber 316 may be used. Temperature ports 340, 342 may be provided in the wall of vessel 310. Temperature sensors 344, 346, such as thermocouples, may be mounted in temperature ports 340, 342 to monitor temperature at various points in chamber 316. Although two temperature ports 340, 342 are shown, any number of temperature ports may be provided. For illustration purposes, temperature ports 340, 342 are provided in sidewall 314. Alternatively, temperature port(s) may be provided in bottom wall 312 in lieu of, or in addition to, providing temperature port(s) in sidewall 314. In the illustrated example, temperature port 340 is positioned nearer the bottom of vessel 310 where heater 320 is arranged, and temperature port 342 is positioned nearer the top of vessel 310. If chamber 316 is uniformly heated, temperature sensors 344, 346 in these temperature ports should output approximately the same temperature readings.

Figure 3B:
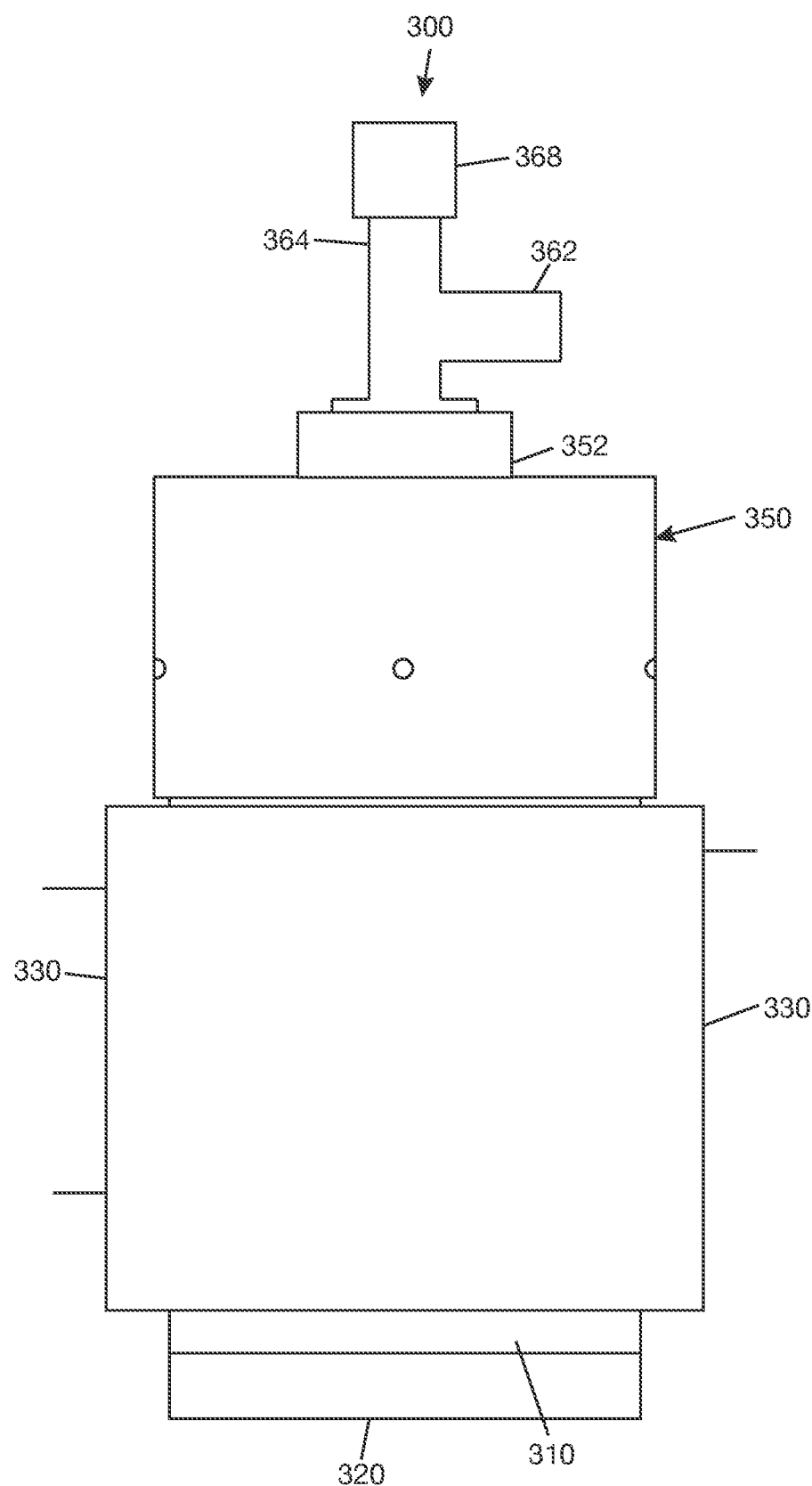
FIG. 3B shows an elevation view of the test chamber shown in FIG. 3A in accordance with one or more embodiments.

Test chamber 300 includes a cap 350 mounted at an open end of vessel 310 so that chamber 316 may be sealed. Cap 350 is removable to allow flexible mold (200 in FIG. 1) to be loaded into chamber 316 and to allow initial filling of chamber 316 with fluid. Cap 350 includes an inner cap member 352, which carries a circumferential seal 354, e.g., an O-ring seal. Seal 354 is positioned to form a seal between inner cap member 352 and vessel 310. Inner cap member 352 includes a bore 356. The bottom end of bore 356 is open to chamber 316. A flow connector 358 is mounted at the top end of bore 352. Flow connector 358 has flow ports 362, 364. Flow port 362 may be connected to a syringe pump (130 in FIG. 1). When initially filling chamber 316 with fluid via flow port 362, flow port 364 is open, and fluid is allowed to fill chamber 316 until the fluid starts spilling out from flow port 364—this ensures that any trapped air in chamber 316 is flushed out. After a period of fluid spilling out of flow port 364, a pressure relief valve 368 (in FIG. 3B) is installed at flow port 364 to seal chamber 316. Pressure relief valve 368 is normally closed. If the pressure in chamber 316 exceeds a certain predetermined pressure, pressure relief valve 368 will open to vent out the excess pressure.

Returning to FIG. 3A, cap 350 may include an outer cap member 370 that is generally coaxial with inner cap member 352. In the example shown, inner cap member 352 is received within a bore of outer cap member 370, and a portion of inner cap member 352 projects above the top end of outer cap member 370. This projecting part of inner cap member 352 includes flow connector 358. Cap 350 may be installed on vessel 310 by mounting inner cap member 352 on the top end of vessel 310. Outer cap member 370 will fit around the outer surface of vessel 310, with a flange portion 352a of inner cap member 352 interposed between outer cap member 370 and the top end of vessel 310. Fasteners 372 can be used to secure outer cap member 370 to vessel 310. Inner cap member 352 may carry a circumferential seal 374, e.g., an O-ring seal, that is positioned to form a seal between inner cap member 352 and outer cap member 370.

A pressure sensor 376 may be installed in sidewall 314 of vessel 310. Pressure sensor 376 may be used to monitor pressure inside chamber 316. In FIG. 1, flow port 362 is connected to syringe pump 130 by a flow line 132. A pressure sensor 134 may be installed in flow line 132 and used to monitor pressure near flow port 362. Pressure readings from either or both of pressure sensors 376, 134 may be used as an indication of pressure inside chamber 316.

Syringe pump 130 is a type of positive displacement pump that can be used to deliver or withdraw precise amounts of fluid. Syringe pump 130 includes a barrel 136 and a plunger 138 inserted into barrel 136. A pusher block 140 is coupled to plunger 138. Pusher block 140 travels along a linear stage 142 that is driven by a motor 144, e.g., a stepper motor or servo motor. For example, linear stage 142 includes a screw that is turned by motor 144, and pusher block 140 moves in a linear direction as the screw is turned. Plunger 138 moves relative to barrel 136 in response to motion of pusher block 140 along linear stage 142. Flow line 132 from flow port 362 is connected to a port 136a in barrel 136, thereby establishing fluid communication between syringe pump 130 and chamber 316. By adjusting the position of plunger 138 relative to barrel 136, fluid can be injected from barrel 136 into chamber 316 or withdrawn from chamber 316 into barrel 136.

Syringe pump 130 may be operated to maintain a desired pressure in chamber 316. In one implementation, system 100 includes a pump controller 150 to adjust a flow rate and flow direction of syringe pump 130 based on an output of pressure sensor 134 and a pressure setpoint from a control system 160. Pump controller 150 may be, for example, a proportional-integral-derivative (PID) controller that is programmed to compare the output of pressure sensor 134 to a pressure setpoint and generate a control for motor 144 if the output of pressure sensor 134 is not the same as the pressure setpoint. If pressure sensor 134 indicates a pressure that is higher than the pressure setpoint, pump controller 150 controls syringe pump 130 to withdraw fluid from chamber 316. If pressure sensor 134 indicates a pressure that is lower than the pressure setpoint, pump controller 150 controls syringe pump to inject fluid into chamber 316. The position of plunger 138 relative to barrel 136 provides an indication of the volume of fluid within barrel 136.

System 300 includes a temperature controller 170 to adjust a heat output of heater 320 of test chamber 300. Temperature controller 170 adjusts the heat output of heater 320 based on an output of temperature sensor 344 and a temperature setpoint from control system 160. Temperature controller 170 may be, for example, a PID controller that is programmed to compare the output of temperature sensor 344 to a temperature setpoint and generate a control for heater 320 if the output of temperature sensor 344 is not the same as the temperature setpoint. Thus, heater 320 is operable or controllable to provide and maintain a desired temperature in chamber 316.

In one implementation, syringe pump 130 is controlled to maintain a certain pressure inside chamber 316. Under this condition, if sample cement 110 expands, syringe pump 130 will need to withdraw fluid from chamber 316 to maintain the certain pressure. Conversely, if sample cement 110 shrinks, syringe pump 130 will need to inject fluid into chamber 316 to maintain the certain pressure. Thus, volumetric changes in sample cement 110 can be correlated to pump volume changes in syringe pump 130 if syringe pump 130 works to maintain a certain pressure inside chamber 316. By "pump volume" in syringe pump 130, we mean the volume of fluid contained in barrel 136 of syringe pump 130 at any given time. The pump volume changes as plunger 138 moves relative to barrel 136. In one implementation, pump volume changes in syringe pump 130 are monitored and used to determine volumetric changes in sample cement 110. Any suitable method for monitoring pump volume changes in syringe pump 130 may be used. For example, the position of plunger 138 may be monitored and used to determine the pump volume at any given time. The position of plunger 138 may be available from pump controller 150 or measured directly by other suitable method.

In one implementation, system 100 includes a data acquisition system 180 that receives and records pump volume data from pump controller 150 or from any other system that measures pump volume of syringe pump 130. Data acquisition system 180 also receives and records pressures and temperatures in chamber 316. In one implementation, data acquisition system 180 receives output signals that are indicative of pressure in chamber 316 from pressure sensor 376. Alternatively, data acquisition system 180 may receive output signals that are indicative of pressure in chamber 316 from pressure sensor 134. In one implementation, data acquisition system 180 receives output signals that are indicative of temperature in chamber 316 from temperature sensor 346. Alternatively, data acquisition system 180 may receive output signals that are indicative of temperature in chamber 316 from temperature sensor 344 or from temperature controller 170. Data acquisition system 180 may be a configurable instrument software such as LabVIEW from National Instruments with appropriate drivers to communicate with sensors. Data acquisition system 180 may record chamber temperature, chamber pressure, and pump volume as a function of time during testing of sample cement 110.

System 100 may include a computer 190 that communicates with data acquisition 180 and control system 160. Computer 190 includes a memory that stores a computer program and a processor to execute instructions of the computer program. The computer program when executed may provide an interface through which a user may indicate testing parameters, such as temperature and pressure setpoints. The computer program may provide the testing parameters to control system 160, which may then communicate the appropriate setpoint to temperature controller 170 and pump controller 150. The computer program may receive data from data acquisition system 180 and may process the data to determine volumetric changes in sample cement 110 as a function of time. The computer program may generate and display one or more plots showing volumetric changes in sample cement 110 as a function of time. The computer program may allow a user to adjust testing parameters at any point during the cement testing.

Figure 4:
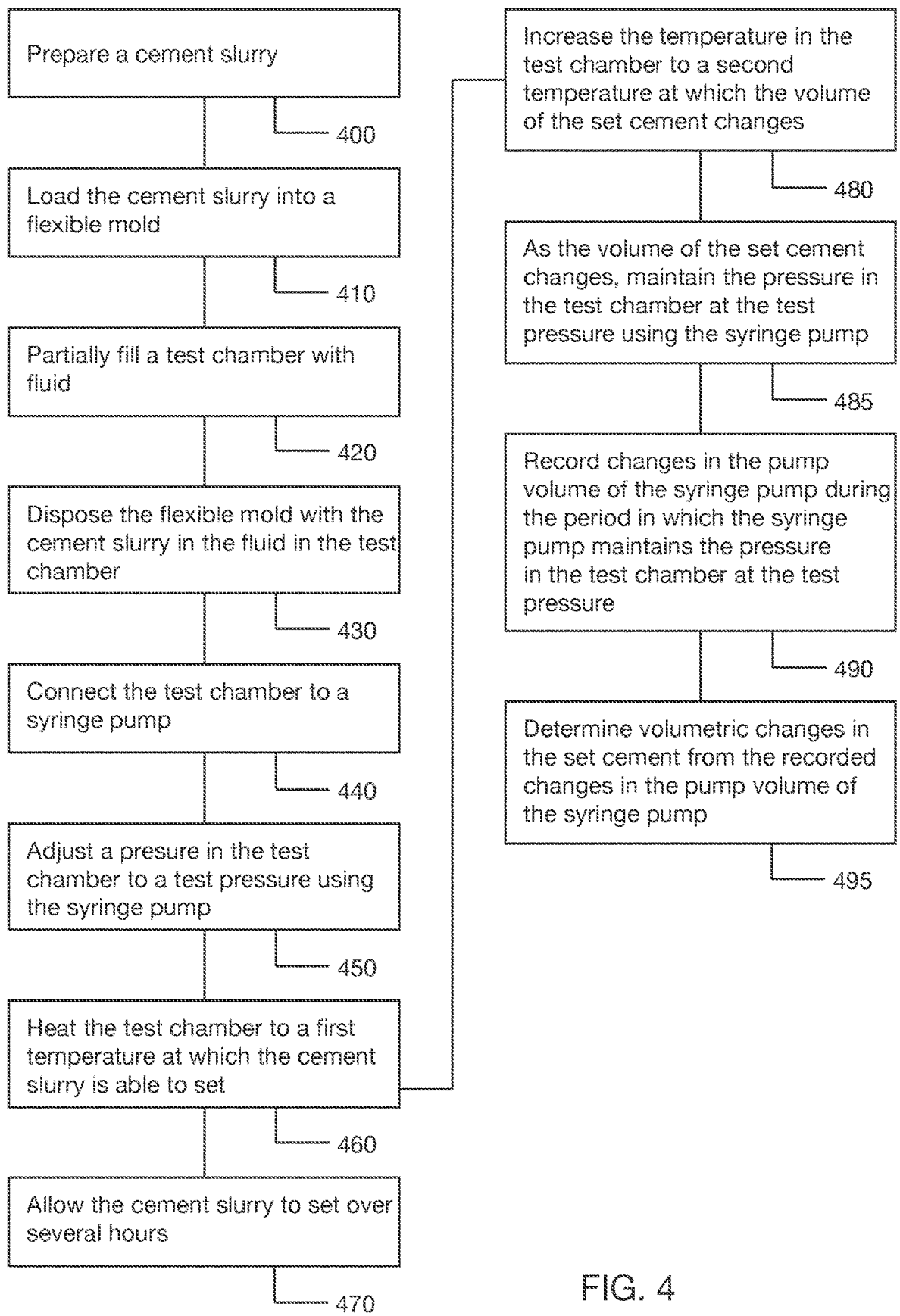
FIG. 4 shows a flowchart of a method of testing a sample cement in accordance with one or more embodiments.

FIG. 4 illustrates a method of measuring volumetric changes in a sample cement using the system described in FIG. 1. At 400, a cement slurry having a cement formulation to be tested is prepared. Such preparation may include providing components of the cement formulation in powder form, combining the different powders and water in a blender, and mixing the powders and water together to form a slurry. In one example, a cement formulation may include a hydraulic cement (i.e., a cement that hardens by hydration) and one or more cement additives. One common type of a hydraulic cement is Portland cement. Both cement class G and class H are typically used for oil and gas applications—classes of cement are defined by the API. In one example, the cement additives may include an expanding additive which when hydrated can trigger expansion of the cement. In one implementation, the expanding additive hydrates at a different temperature compared to a temperature at which the cement sets. This allows volumetric changes in the cement to be measured separately from setting of the cement. In one example, the cement is formulated such that it sets at a lower temperature than a temperature at which the expanding additive becomes hydrated. Other additives to control free water and prevent solids from settling may be included in the cement formulation.

In one non-limiting example, a cement formulation includes a hydraulic cement, such as Portland cement, magnesium oxide (MgO) as expanding additive, and free water cement additive. The cement formulation sets at about 40° C., and expansion of the cement is triggered at about 80° C. However, these temperatures are not intended to be limiting since different types of cement formulations can be prepared with different properties. Also, cement formulations that do not include an expanding additive may be prepared, e.g., if it is desired to study a sample cement without expanding additive. The system described in FIG. 1 is flexible enough to handle cement formulations with or without expanding additive.

At 410, the cement slurry is loaded into the flexible mold. Loading the cement slurry into the flexible mold may include installing the plug (220 in FIG. 2A) at the bottom of the tube (210 in FIG. 2A). Injecting the cement into the bore (214 in FIG. 2A) of the tube, e.g., using a syringe, and then installing the plug (222 in FIG. 2A) at the top of the tube. Both plugs are secured in place. At 420, the chamber (316 in FIG. 3A) of the test chamber (300 in FIG. 3A) is partially filled with fluid, e.g., water. As an example, about 90% of the volume of chamber may be filled with fluid. At 430, the flexible mold with the cement slurry is disposed in the fluid inside the chamber. At 440, the chamber is connected to the syringe pump (130 in FIG. 1) through a flow line (132 in FIG. 1). At 450, the pressure in the chamber is adjusted to a test pressure using the syringe pump. This may include the control system (160 in FIG. 1) providing a pressure setpoint to the pump controller (150 in FIG. 1), which then controls the syringe pump to provide and maintain the test pressure indicated by the pressure setpoint in the chamber. The test pressure is greater than atmospheric pressure and may be determined by a downhole condition to be tested. In one example, the test pressure may be 70 bars (1,000 psi). At 460, the chamber is heated to a first temperature within a first temperature range. The first temperature range is a range of temperatures at which the cement slurry sets. In one example, the cement slurry includes an expanding additive, and the first temperature is below a temperature at which the expanding additive starts to hydrate or becomes active. At 460, the control system may provide a first temperature setpoint to the temperature controller (170 in FIG. 1), which then controls the heater (320 in FIG. 1) to provide and maintain the first temperature in the chamber.

At 470, the cement is allowed to set at the first temperature and test pressure conditions for several hours, e.g., at least 4 hours and up to 24 hours. After the cement has set, at 480, the temperature in the chamber is increased to a second temperature within a second temperature range. In one implementation, the second temperature range is greater than the first temperature range. In one example, the second temperature may be a temperature at which an expanding additive in the cement starts to hydrate. At 480, the control system may provide a second temperature setpoint to the temperature controller, which then controls the heater to provide and maintain the second temperature in the chamber.

Once the expanding additive starts to hydrate, expansion of the set cement will be triggered. At 485, as the volume of the set cement changes, the pressure in the chamber is maintained at the test pressure using the syringe pump. If the set cement is expanding, the syringe pump will withdraw fluid from the chamber so that the pressure in the chamber can be maintained at the test pressure. The amount of fluid withdrawn will depend on the volumetric change in the set cement. On the other hand, if the set cement is shrinking, the syringe pump will inject fluid into the chamber so that the pressure in the chamber can be maintained at the test pressure.

At 490, as the syringe pump acts to maintain the pressure in the chamber at the test pressure, changes in the pump volume of the syringe pump are recorded. At 495, the volumetric changes in the set cement are determined from the pump volume data recorded at 490. If it is desired to investigate the set cement at another pressure, the control system can send a different pressure setpoint to the pump controller, and the method can be repeated from 450 to 495. If it is desired to investigate the set cement at a different temperature, the control system can send a different temperature setpoint to the temperature controller, and the method can be repeated from 460 to 495. In this way, the system allows for interactive temperature and pressure control during testing of a sample cement.

In some cases, the exact temperature at which the expanding additive starts to hydrate may not be known ahead of time. In this case, at 480, the temperature of the chamber may be increased to an initial second temperature that is greater than the first temperature but not necessarily the temperature at which the expanding additive starts to hydrate. Then, the temperature of the chamber may be ramped up during 485, and the response of the cement sample may be observed from the data collected at 490. When expansion of the sample cement is first observed, ramping up of the temperature of the chamber at 485 can be stopped. The temperature when expansion of the sample is first observed can be maintained in the test chamber for the remainder of 485.

Figure 5:
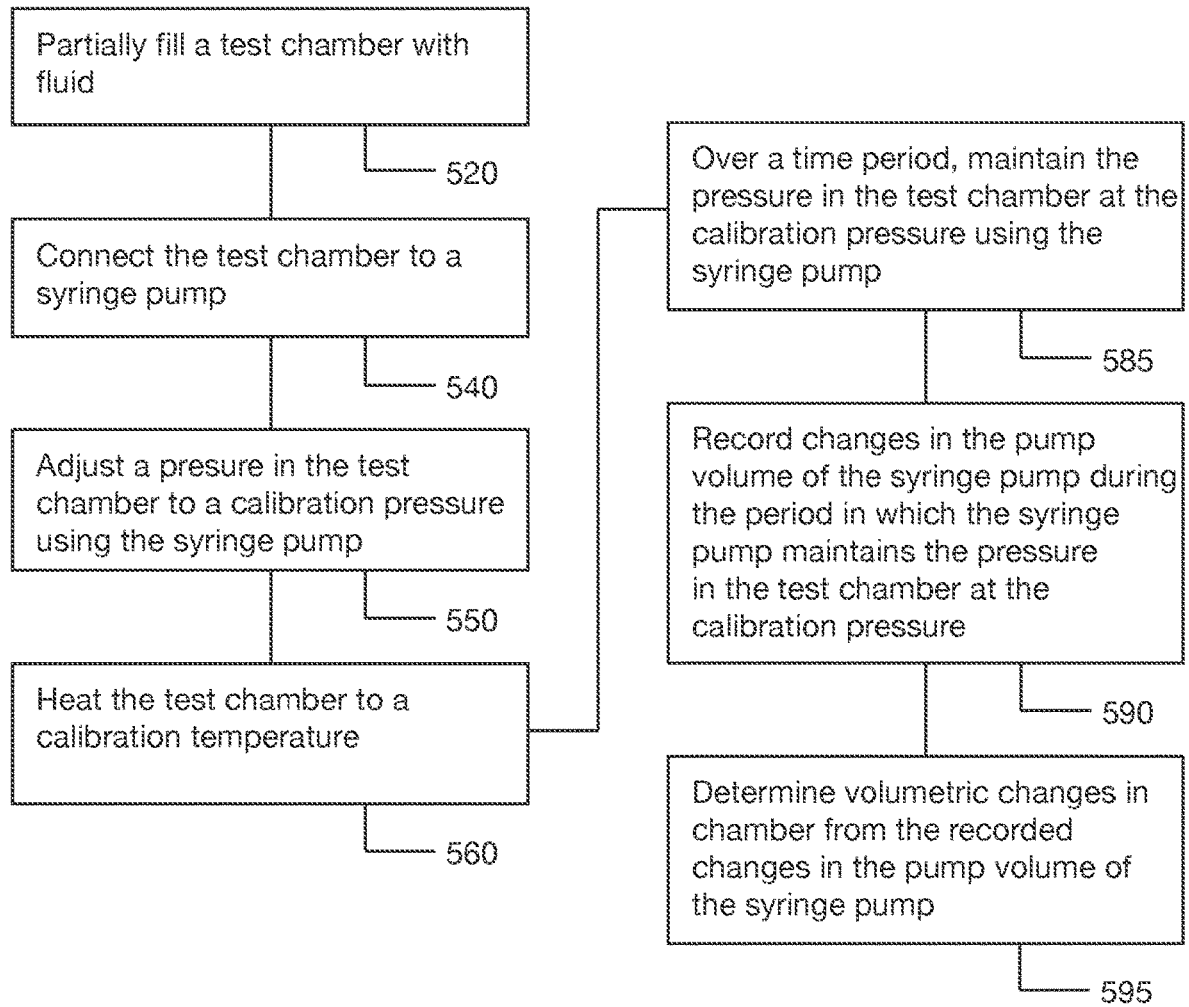
FIG. 5 shows a flowchart of a method of calibrating the system of FIG. 1 to account for micro-leakages in accordance with one or more embodiments.

Prior to making measurements on a sample cement using the system described in FIG. 1, the system may be calibrated to account for any micro-leakages that may affect the results of the measurement. The calibration method is shown in FIG. 5. At 520, the test chamber is partially filled with fluid. At 540, the test chamber is connected to the syringe pump. At 550, the pressure in the test chamber is adjusted to a calibration pressure using the syringe pump. The calibration pressure can be any pressure greater than ambient pressure. At 560, the test chamber is heated to a calibration temperature. The calibration temperature can be any temperature greater than room temperature. In general, the calibration pressure and temperature may be selected to be close to actual testing pressure and temperature. At 585, over a time period, the pressure in the test chamber is maintained at the calibration pressure using the syringe pump. At 590, changes in the pump volume of the syringe during the time period in which the syringe pump maintains the calibration pressure in the test chamber are recorded. At 595, the volumetric changes in the test chamber are determined from the recorded pump volume data. Since there is no sample cement in the test chamber that should create volume changes inside the test chamber, the volumetric changes in the test chamber over the time period should be 0 mL If this is not the case, then there are micro-leakages in the system. In the case of micro-leakages in the system, the absolute value of the gradient of the volumetric changes in the test chamber over time can be calculated. Data collected with a flexible mold and cement sample (495 in FIG. 4) can be corrected using the calculated gradient to account for any leakage.

Figure 6:
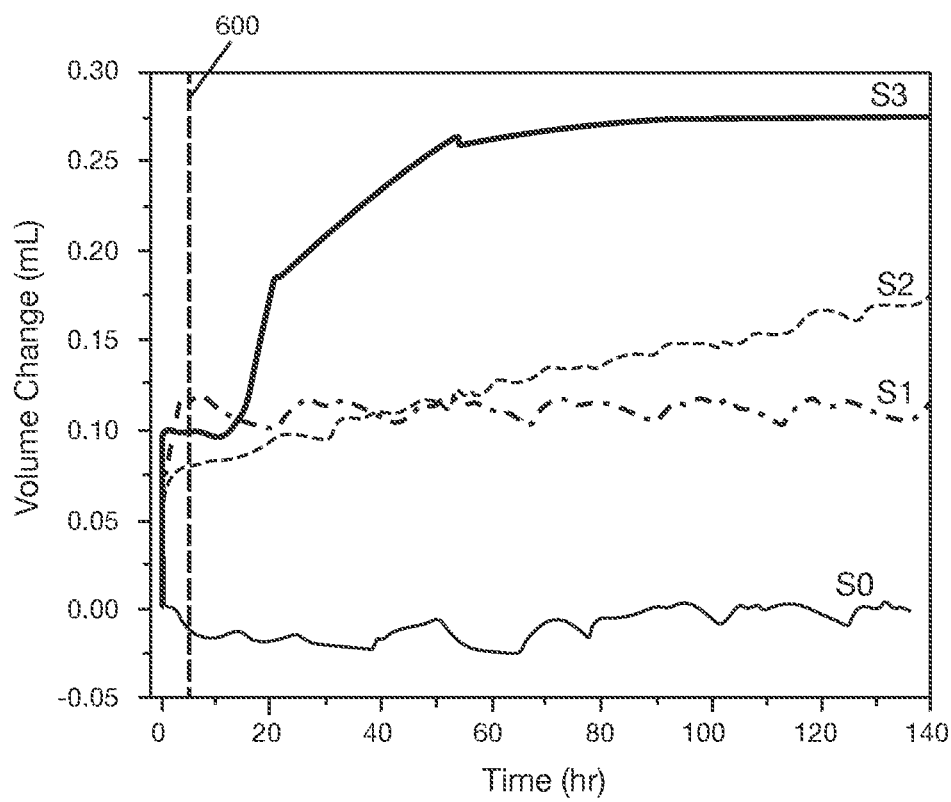
FIG. 6 shows time-dependent volumetric changes in sample cements in accordance with one or more embodiments.

FIG. 6 is a plot showing volumetric changes over time for four different sample cements. Three of the sample cements (S1, S2, S3) included 3% MgO as an expanding additive, and one of the sample cements (S0) did not include an expanding additive. The cement slurry prepared for each sample cement was allowed to set at 40° C. for several hours. Then, the temperature of the test chamber was increased to 60° C. and ramped from 60° C. to 80° C. over 4 hours. The temperature was held at 80° C. for the remainder of the test. The test pressure was set to 1000 psi. The results show that expansion of the sample cements with MgO started when the temperature of the chamber was at about 80° C. (line 600 in FIG. 6). Sample cements S1, S2, S3 experienced volumetric expansion of 0.68%, 1.04%, and 1.63%, respectively. Comparative sample cement S0 without MgO experienced volume shrinkage of 0.15% over the test period.

Figure 7:
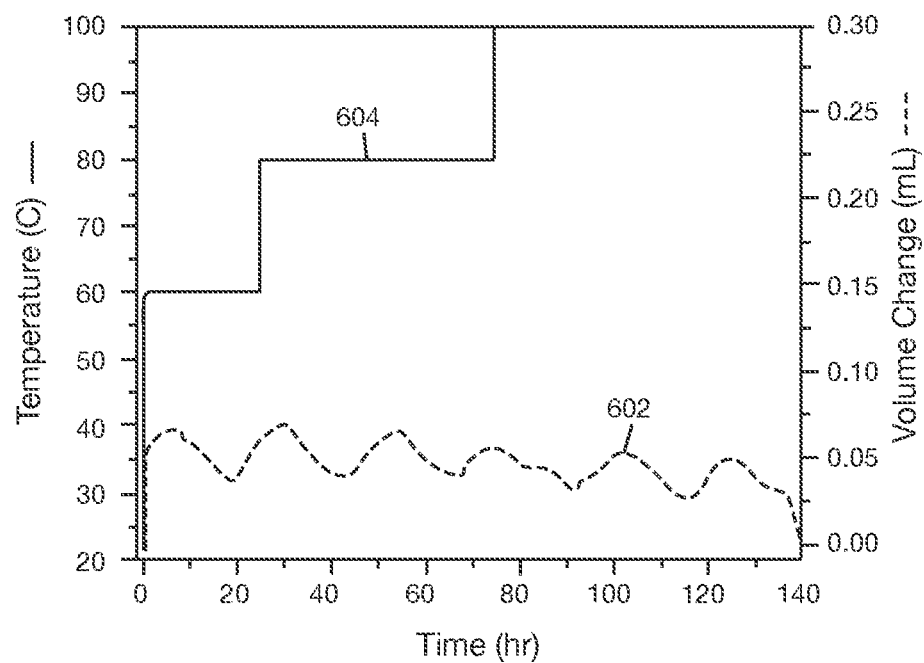
FIG. 7 shows time-dependent volumetric changes in a test chamber without sample cement in accordance with one or more embodiments.

FIG. 7 is a plot showing volumetric changes in the test chamber during a calibration procedure (see 602 in FIG. 7). The calibration pressure was 1000 psi. Calibration temperature was increased to 60° C., then 80° C., and finally to 100° C. (see 604 in FIG. 7). The calibration period was 140 hours. The results show that at 80° C., the system has a leakage of 0.0008 mL/hr. This leakage rate can be used to correct measurements made with an actual sample cement under conditions similar to the calibration conditions.

While the invention has been described with respect to a limited number of embodiments, those skilled in the art, having the benefit of this disclosure, will appreciate that other embodiments can be devised that do not depart from the scope of the invention as described herein. Accordingly, the scope of the invention should be limited only by the accompanying claims.

What is claimed is:

1. A method of testing cement, the method comprising:
loading a cement slurry into a flexible mold;
disposing the flexible mold in a column of fluid comprising a fluid column volume around the flexible mold in a test chamber;
arranging a heater to provide heat to the test chamber;
connecting a first temperature sensor to a first temperature port in the test chamber;
connecting a temperature controller in communication with the first temperature sensor;
connecting a pump in fluid communication with the test chamber, wherein the pump is configured to apply fluid volume adjustments comprising injecting fluid volume to the fluid column volume and withdrawing fluid volume from the fluid column volume;
connecting a first pressure sensor to a pressure port in the test chamber;
connecting a pump controller in communication with the pump and with the first pressure sensor;
connecting a control system in communication with the pump controller and the temperature controller;
adjusting, using the pump controller, a flow rate and flow direction of the pump to apply the fluid volume adjustments to the fluid column volume in response to a difference in pressure from an output of the first pressure sensor between the test chamber and a pressure setpoint from the control system,
adjusting, using the temperature controller, a heat output of the heater in response to a first temperature difference from an output of the first temperature sensor between the test chamber and a first temperature setpoint from the control system, the first temperature setpoint being a temperature at which the cement slurry sets;
maintaining the temperature of the column of fluid at the first temperature setpoint for a first time period, the first time period being a time period in which the cement slurry sets to form a set cement;
adjusting, using the temperature controller, the heat output of the heater in response to a second temperature difference from the output of the first temperature sensor between the test chamber and a second temperature setpoint from the control system,
wherein the second temperature setpoint is greater than the first temperature setpoint, the second temperature setpointrange being a temperature at which an expanding additive in the cement starts to hydrate;
determining, using a computer comprising a processor wherein the computer is connected to the control system, volumetric changes in the set cement over at least a portion of a second time period based on the fluid volume adjustments applied by the pump to the column of fluid in the test chamber; and
correcting the volumetric changes using a calculated gradient based on calibration volume changes over a calibration time period, a calibration pressure, and a calibration temperature.

2. The method of claim 1, wherein the cement slurry comprises a hydraulic cement and the expanding additive, and wherein the expanding additive triggers expansion of the set cement when the set cement has a temperature at the second temperature setpoint.

3. The method of claim 1, wherein applying the fluid volume adjustments to the column of fluid comprises withdrawing fluid from the test chamber as the set cement expands.

4. The method of claim 1, wherein withdrawing fluid from the test chamber as the set cement expands comprises measuring a pressure of fluid in the test chamber and controlling the pump to withdraw fluid from the test chamber in response to the difference in pressure from the output of the first pressure sensor between the test chamber and the pressure setpoint.

5. The method of claim 1, wherein determining the volumetric changes in the set cement over the at least a portion of the second time period comprises determining a volume of fluid withdrawn from the test chamber over the at least a portion of the second time period.

6. The method of claim 1, further comprising, during an initial portion of the second time period, increasing the temperature of the column of fluid in the test chamber to a temperature at which the expanding additive starts to hydrate.

7. The method of claim 1, wherein applying the fluid volume adjustments to the column of fluid comprises selectively injecting fluid into and withdrawing fluid from the test chamber by a syringe pump.

8. The method of claim 1, wherein determining the volumetric changes in the set cement over the at least a portion of the second time period comprises measuring changes in a pump volume of the pump.

9. The method of claim 1, further comprising maintaining the temperature at the second temperature setpoint over the second time period.

10. The method of claim 1, wherein adjusting a pressure of the column of fluid in the test chamber to a set pressure comprises pumping fluid into the column of fluid at the pressure setpoint.

11. A system for testing cement, the system comprising:
a flexible mold to hold a cement slurry;
a test chamber to hold a column of fluid comprising a fluid column volume around the flexible mold;
a heater arranged to provide heat to the test chamber;
a first temperature sensor connected to a first temperature port in the test chamber;
a temperature controller in communication with the first temperature sensor;
a pump in fluid communication with the test chamber, wherein the pump is configured to apply fluid volume adjustments comprising injecting fluid volume to the fluid column volume and withdrawing fluid;
a first pressure sensor connected to a pressure port in the test chamber;
a pump controller in communication with the pump and with the first pressure sensor;
a control system in communication with the pump controller and the temperature controller,
wherein the pump controller is configured to adjust a flow rate and flow direction of the pump to apply the fluid volume adjustments to the fluid column volume in response to a difference in pressure from an output of the first pressure sensor between the test chamber and a pressure setpoint from the control system,
wherein the temperature controller is configured to adjust a heat output of the heater in response to a first temperature difference from an output of the first temperature sensor between the test chamber and a first temperature setpoint from the control system, the first temperature setpoint being a temperature at which the cement slurry sets,
wherein the temperature controller is configured to maintain the temperature of the column of fluid at the first temperature setpoint for a first time period, the first time period being a time period in which the cement slurry sets to form a set cement,
wherein the temperature controller is configured to adjust the heat output of the heater in response to a second temperature difference from the output of the first temperature sensor between the test chamber and a second temperature setpoint from the control system,
wherein the second temperature setpoint is greater than the first temperature setpoint, the second temperature setpoint being a temperature at which an expanding additive in the cement starts to hydrate; and
a computer comprising a processor, wherein the computer is connected to the control system and configured to:
determine volumetric changes in the set cement over at least a portion of a second time period based on the fluid volume adjustments applied by the pump to the column of fluid in the test chamber; and
correct the volumetric changes using a calculated gradient based on calibration volume changes over a calibration time period, a calibration pressure, and a calibration temperature.

12. The system of claim 11, wherein the flexible mold comprises a tube having a wall made of a flexible material.

13. The system of claim 11, wherein the flexible mold comprises an elastomeric material.

14. The system of claim 11, wherein the flexible mold further comprises permeable plugs removably mounted at opposite ends of the flexible mold.

15. The system of claim 11, wherein the flexible mold further comprises impermeable plugs removably mounted at opposite ends of the flexible mold.

16. The system of claim 11, wherein the pump is a syringe pump.

17. The system of claim 11, further comprising a second temperature sensor connected to a second temperature port, in the test chamber, wherein the temperature controller is in communication with the second temperature sensor.

18. The system of claim 11, further comprising a second pressure sensor connected to a second pressure port in the test chamber,
wherein the pump controller is in communication with the second pressure sensor.

19. The system of claim 11, further comprising:
a user device coupled to the control system,
wherein the user device is configured to provide an interface for displaying testing parameters,
wherein the testing parameters comprise temperature setpoints and pressure setpoints, and
wherein the control system:
  receives the testing parameters from the processor;
  communicates the temperature setpoints to the temperature controller;
  communicates the pressure setpoints to the pump controller;
  receives, from a data acquisition system, received data regarding the testing parameters;
  compares, using the processor, the received data with parameter ranges of the testing parameters, and then calculates a comparison result;
  determines, using the processor and the comparison result, test parameter conformances; and
  generates, using the processor, plotted data comprising the test parameter conformances;
wherein the control system comprises the processor, the control system comprising functionality for correcting, using the processor, the volumetric changes using the calculated gradient determined by the control system using the calibration volume changes over the calibration time period, the calibration pressure, and the calibration temperature.

20. The system of claim 19,
wherein the received data comprises the output of the first pressure sensor and the output of the first temperature sensor; and
wherein the test parameter conformances comprise at least one of:
  a satisfactory conformance comprising the differences between the testing parameters and the received data satisfy the parameter ranges, and
  a non-satisfactory conformance comprising the differences between the testing parameters and the received data fail to satisfy the parameter ranges;
wherein the user device is further configured to:
  display the test parameter conformances, and
  obtain a user selection of one or more adjusted test parameters in response to displaying the test parameter conformances.

* * * * *